(12) United States Patent
Höök et al.

(10) Patent No.: US 9,784,746 B2
(45) Date of Patent: *Oct. 10, 2017

(54) METHOD FOR STUDYING TRANSPORT OF AN AGENT ACROSS A BILAYER MEMBRANE IN BIOANALYTICAL SENSOR APPLICATIONS

(71) Applicant: Bio-Rad Laboratories, Inc., Hercules, CA (US)

(72) Inventors: Fredrik Höök, Alingsås (SE); Magnus Brändén, Göteborg (SE); Seyed Tabaei, Göteborg (SE)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/131,956

(22) Filed: Apr. 18, 2016

(65) Prior Publication Data
US 2016/0231326 A1 Aug. 11, 2016

Related U.S. Application Data

(60) Division of application No. 14/258,932, filed on Apr. 22, 2014, now Pat. No. 9,322,830, which is a
(Continued)

(51) Int. Cl.
*G01N 21/41* (2006.01)
*G01N 21/552* (2014.01)
(Continued)

(52) U.S. Cl.
CPC .............. *G01N 33/68* (2013.01); *G01N 21/41* (2013.01); *G01N 21/553* (2013.01); *G01N 33/50* (2013.01);
(Continued)

(58) Field of Classification Search
None
See application file for complete search history.

(56) References Cited

U.S. PATENT DOCUMENTS 9,322,830 B2 * 4/2016 Hook ................. G01N 33/5432
2011/0008902 A1 1/2011 Hook

FOREIGN PATENT DOCUMENTS

WO WO 2004/090165 A1 * 10/2004

OTHER PUBLICATIONS

William R. Hargreaves, David W. Deamer "Liposomes from ionic, single-chain amphiphiles," Biochemistry, 1978, 17 (18), pp. 3759-3768.*
(Continued)

*Primary Examiner* — Yelena G Gakh
*Assistant Examiner* — Michelle Adams
(74) *Attorney, Agent, or Firm* — Holland & Hart LLP

(57) ABSTRACT

The present invention provides a method for studying transport of an agent across a membrane comprising the steps a) providing at least one surface with a bilayer structure tethered to the surface, said bilayer structure comprising a detection volume, b) contacting the bilayer with at least one agent to be analyzed, and c) detecting a change in refractive index in the detection volume resulting from transportation of the agent across the membrane. Further there is provided a device comprising a) at least one surface, b) at least one bilayer structure tethered to the surface, and c) at least one sensor capable of detecting a change in refractive index in a detection volume, wherein the bilayer structure encloses a first volume of the detection volume and wherein the volume not enclosed by the bilayer structure but within the detection volume is a second volume and wherein the ratio between the first volume and second volume is above about 0.001.

30 Claims, 6 Drawing Sheets

Related U.S. Application Data continuation of application No. 12/863,499, filed as application No. PCT/SE2009/050123 on Feb. 6, 2009, now abandoned.

(60) Provisional application No. 61/027,352, filed on Feb. 8, 2008.

(51) Int. Cl.
*G01N 33/68* (2006.01)
*G01N 33/543* (2006.01)
*G01N 33/50* (2006.01)
*G01N 33/92* (2006.01)
*G01N 21/21* (2006.01)
*G01N 21/25* (2006.01)

(52) U.S. Cl.
CPC ... *G01N 33/5432* (2013.01); *G01N 33/54353* (2013.01); *G01N 33/54373* (2013.01); *G01N 33/6872* (2013.01); *G01N 33/92* (2013.01); *G01N 21/211* (2013.01); *G01N 2021/258* (2013.01); *G01N 2333/43565* (2013.01); *G01N 2500/00* (2013.01)

(56) References Cited

OTHER PUBLICATIONS

Cheryl L Baird, Elizabeth S Courtenay, David G Myszka "Surface plasmon resonance characterization of drug/liposome interactions," Analytical Biochemistry vol. 310, Issue 1, Nov. 1, 2002, pp. 93-99.*

* cited by examiner

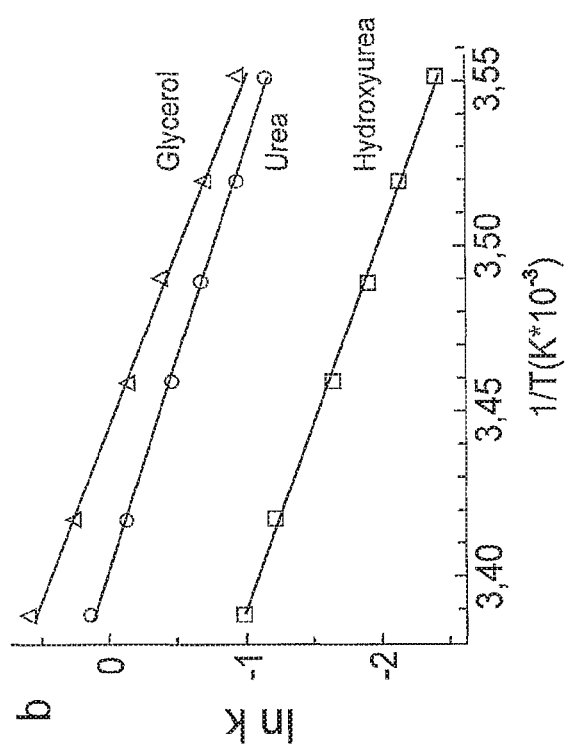
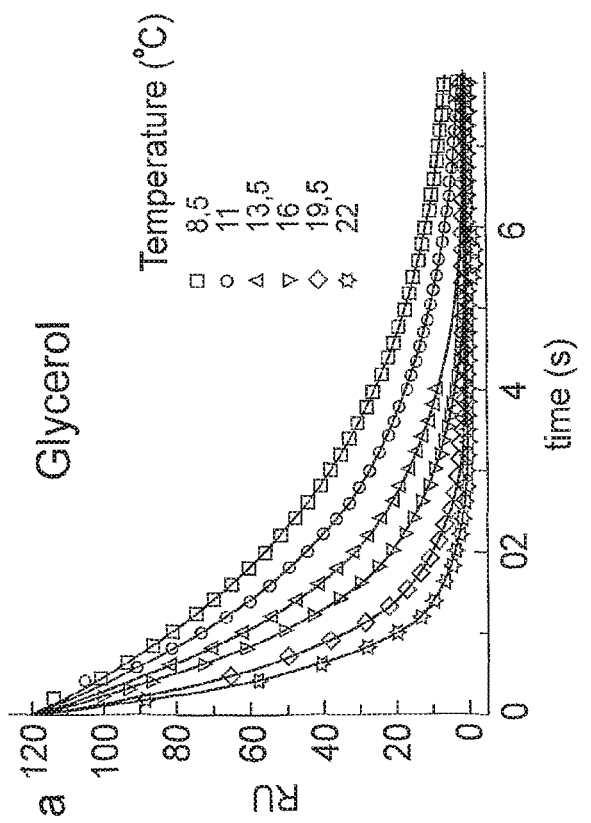
Fig.5A
Fig.5B

METHOD FOR STUDYING TRANSPORT OF AN AGENT ACROSS A BILAYER MEMBRANE IN BIOANALYTICAL SENSOR APPLICATIONS

CROSS-REFERENCE TO RELATED PATENT APPLICATIONS

This is a division of U.S. patent application Ser. No. 14/258,932, titled "Method for Studying Transport of an Agent Across a Bilayer Membrane in Bioanalytical Sensor Applications," filed on 22 Apr. 2014 and published at U.S. Patent App. Pub. No. 2015/0031139, which is a continuation of U.S. patent application Ser. No. 12/863,499, titled "Method and Device for Studying Transport of an Agent Across a Bilayer Membrane in Bioanalytical Sensor Applications," filed on 27 Sep. 2010 and published at U.S. Pat. App. Pub. No. 2011/0008902, which is a national stage of International Patent Application No. PCT/SE2009/50123 titled "Method and Device for Studying Transport of an Agent Across a Bilayer Membrane in Bioanalytical Sensor Applications," filed on 6 Feb. 2009 and published as International Pub. No. WO 2009/099391, which claims priority to U.S. Provisional Patent App. No. 61/027,352, titled "Method and Device for Studying Transport of an Agent Across a Bilayer Membrane in Bioanalytical Sensor Applications," filed on 8 Feb. 2008; all of which are expressly incorporated herein by reference in their entireties.

The present invention relates to a method and a device for the measurement of transport of an agent across a bilayer membrane.

BACKGROUND

Transport across membranes and the influence of molecules associated with a membrane such as membrane proteins are important to study for instance when developing new drugs and also in many other contexts.

In 1895 Overton suggested that molecules permeate the cells in the same relative order as their oil-water partition coefficient [1] and in 1943 Danielli proposed that a continuous lipid bilayer acts as a diffusion barrier determining the rate of passive diffusion across cellular membranes [2]. However, the first means to directly study permeation across an isolated lipid bilayer became available in the early 60-ies through the development of means to prepare single lipid bilayers separating two aqueous compartments [3]. While this technique is well suited for permeability studies of charged solutes, the standard approach of today for studies of passive and active transport of non-electrolytes, including water transport and drug uptake, relies on measurements of osmotic-induced size changes of suspended lipid vesicles (so called liposomes) [4]. This method is based on dynamic light scattering (DLS) measurements of variations in scattered light intensity as the liposome dimension changes in response to osmotically induced water transfer across the lipid membrane, upon which the liposomes first (<1 ms) shrink, as water diffuse out of the liposomes, and subsequently swell as water reenters the liposomes driven by the inward permeation of solute molecules [5]. Although successfully applied in numerous studies on the nature of passive and active solute permeation [6], the method is restricted by the fact that a change in liposome size is an indirect effect, which does not necessarily correlate with the actual solute transport. In addition, since not only the liposome size, but also liposome motion, solute refractive index, and membrane aggregation contribute to the intensity of the scattered light, the quantification of solute transfer is not always straightforward [7,8]. From a practical perspective, this methods also suffers from low signal-to-noise ratios, which means that averaging from multiple data series is generally required to resolve kinetic traces. Furthermore, since measurements are performed on suspended liposomes, the method is not compatible with parallel or sequential screening of the very same liposome sample. This, in turn, means that substantial amounts of material are generally needed. Besides somewhat improved sensitivities, these limitations holds also for a less wide-spread method, in which osmotically induced liposome size fluctuations are recorded by monitoring changes in self-quenching of liposome-entrapped fluorophores upon liposome shrinkage and concomitant increase in fluorophore concentration [9].

The possibility to screen multiple recognition events either sequentially or simultaneously is one of the main advantages of surface-based bioanalytical sensor technologies, where the very same set of surface-immobilized probe molecules is exposed to a series of different compounds in an automated fashion. An additional reason for the emerging importance of these sensors in life-science stems from the fact that they can be combined with micro-fluidic handling [10], which makes them compatible with small sample volumes and thus well suited for measurements on rare and non-abundant substances. Surface plasmon resonance (SPR) is today the dominating surface-based bioanalytical sensor. It is based on excitation of laterally propagating surface plasmons at planar metal (usually gold) substrates, where the condition for SPR excitation is extremely sensitive to changes in interfacial refractive index, $\Delta n_{interface}$ induced by for example biomolecular binding within a region in close proximity to the surface (typically hundreds of nanometers). Hence, by immobilizing probe molecules on the surface, binding of targets to the immobilized probes can be monitored in real time via a response which to a good approximation is proportional to $\Delta n_{interface}$ [11, 12].

Other known devices for studying transport across membranes include liposomes in a solution. To the liposome membrane there are associated for instance a membrane protein of interest and the membrane protein mediated transport of an agent across the membrane is studied using methods involving for instance fluorescence and/or radioactivity measurements.

US 2004/0033624 disclose a membrane receptor reagent and assay device. Liposomes are tethered to a surface with anchor groups. The surface comprises reagent ligands that are tethered to the surface. The ligands are able to bind reversibly to a receptor in the liposome membrane. The membrane protein in the liposome is associated with a molecule with the capability to be excited by emitted energy from the surface and thereby produces a detectable signal. The binding of the membrane protein in the liposome membrane to the reagent ligands on the surface tend to pull the liposomes towards the surface. A test molecule with affinity to the membrane protein will bind competitively to the membrane protein and to some extent replace the reagent ligand on the surface. This will result in that membrane proteins come off the surface and are redistributed in the liposome membrane, while the liposome still is anchored to the surface. The membrane proteins will have a larger average distance from the surface and thereby they receive less energy from the surface, since the energy transfer from the surface is distance dependent. This can be detected. The method in US 2004/0033624 requires some kind of label such as a fluorophore in order to function.

In the assays for the measurement of membrane protein mediated transport across a membrane according to the state of the art, there is room for an improvement regarding the amount of membrane protein that has to be used. Membrane proteins are often difficult and expensive to purify in substantial quantities.

In the state of the art there is also room for improvement because a label has to be used in many assays. Labelling is not always possible since it may alter the structure and function of the analyte/receptor and interfere with the molecular interaction that is to be investigated. In addition fluorescent markers are hydrophobic, which can cause unspecific background binding.

SUMMARY OF THE INVENTION

It is an object of the present invention to address at least some of the disadvantages associated with known analysis methods and devices for measuring transport across membranes, and to provide an improved method and device, alleviating at least some of the problems in the prior art. Further disadvantages associated with known methods and devices and the advantages associated with the embodiments of the present invention will be apparent to a skilled person upon a closer study of the description, example and claims.

There is disclosed a method and device as defined in the claims, incorporated herein by reference.

Further aspects of the invention, as well as their advantages, will become evident to the skilled person upon closer study of the description, example, claims and drawings.

DEFINITIONS

Before the present device and method are described in detail, it is to be understood that this invention is not limited to the particular configurations, method steps, detection methods, transducing methods, sensors and materials disclosed herein as such configurations, method steps, detection methods, transducing methods, sensors and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an", and "the" include plural referents unless the context clearly dictates otherwise. Thus, for example, a reference to a reaction mixture containing "an analyte" includes a mixture of two or more analytes.

The term "about" when used in the context of numeric values denotes an interval of accuracy, familiar and acceptable to a person skilled in the art. Said interval is preferably ±10%.

In describing and claiming the present invention, the following terminology will be used in accordance with the definitions set out herein.

The term "bilayer structure" as used throughout the description and the claims denotes a double layer structure of atoms or molecules and especially lipids. The term encompasses bilayers of all geometries including but not limited to curved bilayers. Examples of bilayer structures include but are not limited to liposomes.

The term "detection volume" as used throughout the description and the claims denotes a volume in which the refractive index is measured.

The term "ellipsometry sensor" as used throughout the description and the claims denotes a sensor comprising an ellipsometer.

The term "ionophore" as used throughout the description and the claims denotes a lipid-soluble molecule with the capability to transport ions across a lipid bilayer.

The term "lipid" as used throughout the description and the claims denotes any fat-soluble molecules. Examples of lipids include but are not limited to; fats, oils, waxes, cholesterol, sterols, monoglycerides, diglycerides, and phospholipids.

The term "liposome" as used throughout the description and the claims denotes an essentially spherical vesicle comprising a lipid bilayer membrane. Liposomes may comprise a core of an aqueous solution. The lipid membrane of the liposome may comprise components such as but not limited to proteins, glycolipids, steriods and other membrane-associated components.

The term "membrane" as used throughout the description and the claims comprises all types of membrane such as but not limited to a bilayer membrane. A membrane may comprise molecules such as but not limited to proteins and lipids.

The term "membrane protein" as used throughout the description and the claims denotes a protein which is associated with a membrane.

The term "sensor" as used throughout the description and the claims denotes a transducer which uses a type of energy, a signal of some sort, and converts it into a reading for the purpose of information transfer.

The term "spacer" as used throughout the description and the claims denotes a molecule that is used to link together other molecules so that there is a space between the linked molecules.

The term "surface" as used throughout the description and the claims should be interpreted in a wide sense. A surface can in the present invention be used to support means on which structures can be tethered.

The term "surface plasmon resonance sensor" as used throughout the description and the claims denotes a sensor utilising the excitation of surface plasmons by light.

The term "tether" as used throughout the description and the claims denotes the attachment or entrapment of a material to a surface in a manner that confines, but not necessarily restricts the movement of the material.

DESCRIPTION OF THE INVENTION

In a first aspect the present invention provides a method for studying transport of an agent across a membrane comprising the steps
  a) providing at least one surface with a bilayer structure tethered to the surface, said bilayer structure comprising a detection volume,
  b) contacting the bilayer with at least one agent to be analysed, and
  c) detecting a change in refractive index in the detection volume resulting from transportation of the agent across the membrane.

The bilayer structure is in contact with a solvent. In one embodiment the solvent is water. The bilayer structure comprises at least one membrane.

In one embodiment at least one membrane protein is associated with the bilayer structure. If it is desired to study transport across a membrane which is mediated by a membrane protein, the membrane protein is in one embodiment inserted in the bilayer membrane. Also transport of other molecules on the transport across a membrane can be studied. Examples include but are not limited to passive diffusion of molecules across membranes and transport which is facilitated by for example ionophores and permeation enhancers. A permeation enhancer is a molecule which is added to the solution comprising the analyte and which influences the transport across the membrane.

In one embodiment at least one entity from the group consisting of a membrane protein, and an ionophore is associated with the bilayer structure.

The surface comprises a detection volume in which the refractive index is measured. The bilayer structure tethered to the surface is entirely or partly within the detection volume. In one embodiment the detection volume is a volume limited by the surface and a plane 250 nm from the surface and parallel to the surface.

In one embodiment the sensitivity of the detection volume decreases exponentially with the distance from the surface. In one embodiment the detection volume is limited to a volume where the detection sensitivity is more than 1% of the maximum sensitivity at the surface. Thus it is possible to calculate a detection volume also for an embodiment where the sensitivity of the detection volume decreases exponentially with the distance from the surface. An example of an embodiment where the sensitivity of the detection volume decreases exponentially with the distance from the surface includes but is not limited to an embodiment comprising a surface plasmon resonance sensor.

The bilayer structure is such that an analyte can not diffuse or move freely across the bilayer structure because of the bilayer. However, the analyte can still pass through the membrane.

In one embodiment the bilayer structure comprises a volume which is at least partly enclosed by the bilayer.

The analyte to be investigated is in one embodiment added to the solvent in contact with the bilayer structure. Depending on the properties of the analyte, it may be transferred very slowly or hardly at all across the bilayer membrane. For some analytes, the analyte may be transferred across the bilayer membrane at a higher rate. The transport of an analyte across the membrane depends on the properties of the analyte and on the molecules in the bilayer.

To the bilayer structure there is in one embodiment associated at least one molecule to be studied. Examples of such molecules include but are not limited to; ionophores, integral membrane spanning proteins, proteins binding to one side of the bilayer through a hydrophobic patch, mainly hydrophilic proteins attaching hydrophobically through a covalently bound alkyl chain, mainly hydrophilic proteins with a hydrophobic pocket that can attract a lipid chain, and hydrophilic proteins binding electrostatically.

The present invention provides a possibility to study transport across a bilayer membrane facilitated by a molecule. The transport of the analyte across the bilayer membrane is measured by measuring the refractive index.

Examples of analytes include but are not limited to positive ions, negative ions, drug molecules, organic molecules, inorganic molecules, receptor ligands, sucrose, DNA, RNA, peptides, and proteins.

In one embodiment an analyte is added to the solvent in contact with the bilayer structure and is spread over a volume which is on one side of the bilayer in the bilayer structure. The analyte dissolved in the solvent at a certain concentration has one refractive index. In the volume on the other side of the bilayer in the bilayer structure the concentration of the analyte may be different, which will give a different refractive index for that volume. By measuring the refractive index it is possible to monitor the transport across the membrane.

Advantages of surface-based techniques include that they better can be combined with micro-fluidic devices, they can be fully automated and measurements require smaller sample volumes In one embodiment the sensor utilises a technique that measures refractive index changes in close proximity to the surface. In one embodiment the sensor has the capability to measure changes in refractive index in the interval 0-250 nm from the surface.

In one embodiment the method comprises detecting a change in refractive index with a sensor selected from the group consisting of a surface plasmon resonance sensor, an ellipsometry sensor, and an optical waveguide laser spectroscopy sensor.

In one embodiment the bilayer structure comprises at least one liposome. In a further embodiment the bilayer structure comprises at least one layer of liposomes. In still a further embodiment the bilayer structure is a layer of tethered liposomes. In another embodiment the bilayer structure comprises at least two layers of liposomes. In yet another embodiment the bilayer structure is a multitude of liposomes tethered to the surface.

In one embodiment the liposomes are tethered to the surface with a spacer molecule. In one embodiment where there are several layers of liposomes there is at least one spacer that tethers the liposomes in one layer to the liposomes in an adjacent layer.

In one embodiment the method comprises measuring the refractive index in a volume enclosed by the bilayer structure.

In one embodiment the method comprises measuring the refractive index in a volume enclosed by liposomes tethered to the surface.

In one embodiment the method comprises measuring the refractive index in a volume enclosed by at least one liposome tethered to the surface.

In one embodiment the bilayer structure encloses a first volume of the detection volume and wherein the volume not enclosed by the bilayer structure but within the detection volume is a second volume and wherein the ratio between the first and second volumes is optimised for measurement of refractive index of the first volume. When it is desired to measure the refractive index of the first volume the first volume should be as large as possible compared to the second volume. A large first volume will give higher sensitivity. Examples of suitable ratios between the first volume and the second volume include but are not limited to 0.001, 0.01, 0.1, 1, and 10. Also higher values of the ratio are encompassed by the present invention such as 20, 50, 100, 500, and 1000.

In conclusion, the presently invented method to study cell-membrane permeation, advantageously admits direct measurements of the transfer rate of both uncharged and charged solutes across biological membranes. The method is based on resolving the temporal change in refractive index upon a permeation-dependent change in the solute concentration inside liposomes confined to the evanescent field associated with, for example, a surface plasmon resonance active sensor surface.

In a second aspect of the present invention there is provided a device comprising;

a) at least one surface, b) at least one bilayer structure tethered to the surface, and c) at least one sensor capable of detecting a change in refractive index in a detection volume, wherein the bilayer structure encloses a first volume of the detection volume and wherein the volume not enclosed by the bilayer structure but within the detection volume is a second volume and wherein the ratio between the first volume and second volume is above about 0.001.

In alternative embodiments the ratio between the first volume and second volume is above about 0.001, preferably above about 0.01, more preferably above about 0.1, even more preferably above about 1, and most preferably above about 10. A high ratio is desired because it leads to a better sensitivity for the refractive index measurement in the first volume. One advantage of the present invention is that the sensitivity and accuracy can be increased by providing a high ratio.

In one embodiment the bilayer structure comprises at least one liposome tethered to the surface. In yet another embodiment the bilayer structure comprises a multitude of liposomes tethered to the surface.

In one embodiment the at least one liposome is tethered to the surface with at least one spacer. Examples of spacers include but are not limited to a polymer, a nucleic acid, DNA, a His-tag, a biotinylated lipid attached to avidin covalently bound to the surface, and hydrophobically modified dextran. Also any combination of the above mentioned spacers can be used.

In one embodiment the at least one spacer is a polymer. In another embodiment the at least one spacer is a His-tag. In a further embodiment the there are both polymer spacers and His-tag spacers.

In one embodiment the distance between the bilayer structure and the surface is less than about 250 nm.

In one embodiment the sensor which measures the refractive index in the detection volume is selected from the group consisting of a surface plasmon resonance sensor, an ellipsometry sensor, and an optical waveguide laser spectroscopy sensor.

In one embodiment the sensor utilizes the phenomenon surface plasmon resonance.

DETAILED AND EXEMPLIFYING DESCRIPTION

Brief Description of the Drawings

FIGS. 5a and 5b show the release and transport rate for glycerol over different temperatures.

Figure 1:
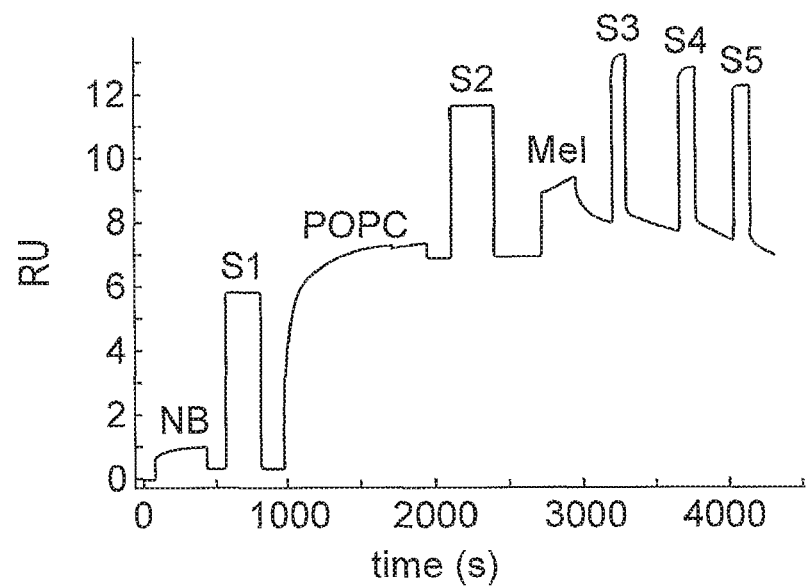
FIG. 1 shows the successive addition of Neutravidin/Biotin DNA (N/B), 0.1 M sucrose (S1), 2 mg/ml cholesterol DNA tagged POPC-liposomes (POPC), 0.1 M sucrose (S2), 40 µM melittin, 0.1 M sucrose (S3), 0.1 M sucrose (S4), 0.1 M sucrose (S5) to a PEG/PEG-biotin functionalized Biacore® sensor.

Example 1, Study of Melittin and its Effect on Membrane Transport

Material and Methods

1-Palmitoyl-2-Oleoyl-sn-Glycero-3-Phophocholine (POPC) was purchased from Avanti Polar Lipids®. PEG-polymers (3 kDa), HS-PEG-NHCO—$CH_2CH_2$—OH (HS-PEG) HS-PEG-NHCO—$CH_2CH_2$-Biotin (HS-PEG-Biotin) were purchased from Rapp Polymere® GmbH. The Sensor chips were purchased from GE Healthcare®. The membrane protein analysis kit came from LayerLab®. HEPES-2 is 10 mM HEPES, 150 mM NaCl, pH 7.4.

Preparation of Liposomes

Liposomes were made by first evaporating the solvent, chloroform, from the POPC lipids using a flow of nitrogen gas. The dried lipids were then kept under the flow of nitrogen gas for at least one hour after which HEPES-2 was added to yield a 4 mg/ml concentration of POPC. The dissolved POPC lipids were vortexed for at least 30 min to yield multi-laminar liposomes. Uni-laminar liposomes were produced using a mini extruder and polycarbonate membranes with pore size of 50 nm from Avanti Polar Lipids® with a 50 nm pore size. The radiuses of the liposomes had a Gaussian size distribution with a mean radius of 36 nm. The liposomes were stored under nitrogen gas at 4° C. until use (within 2 days).

Functionalization of the Biosensor Surface

A mixture (300 µl) of HS-PEG (200 µg/ml) and HS-PEG-Biotin (20 µg/ml), dissolved in HEPES-2, were injected over the Biacore® Au sensor chip at a flow rate of 5 µl/min. Then a mixture (150 µl) of NeutrAvidin (40 µg/ml) and Biotin-DNA (0.7 µM) was injected and bound to HS-PEG-Biotin at the surface.

Tethering of Liposomes

POPC liposomes (2 mg/ml, in HEPES-2) containing cholesterol-DNA tags (3 DNA tags per liposome) were injected at a flow rate of 5 µl/min. The end of the DNA-part of the cholesterol-DNA tag is single-stranded and complementary in sequence to the Biotin-DNA at the surface enabling tethering of the liposomes to the sensor surface.

Melittin Binding to the Liposomes

The reversible binding of melittin was measured in the Biacore® instrument directly after the tethering of POPC liposomes was finished. Melittin solutions at a concentration of 0.5-40 µM in HEPES-2 were injected in sequence. During injection the melittin molecules bind to the liposomes and after the injection is terminated, running buffer (HEPES-2) flows over the surface and melittin dissociates. After the dissociation was complete a new melittin solution of different concentration was injected.

Rupture of Liposomes by Melittin

Rupture of liposomes by melittin was measured in the Biacore® instrument directly after the tethering of POPC liposomes. Melittin dissolved in HEPES-2 at a concentration of 360 µM (1 mg/ml) was injected and the decrease in response (RU) as the liposomes rupture was monitored.

Melittin Mediated Uptake of Sucrose

After tethering of NeutrAvidin/Biotin-DNA the following injections were made in sequential order; 0.1 M sucrose, 2 mg/ml cholesterol-DNA tagged POPC-liposomes, 0.1 M sucrose, 40 µM melittin, 0.1 M sucrose, 0.1 M sucrose, 0.1 M sucrose. All samples were dissolved in HEPES-2.

Results

Tethering of Liposomes

There was binding of liposomes to the biosensor surface. The Carboxylic groups at the surface were activated for amide binding using EDC/NHS. Thereafter PLL-PEG/PLL-PEG-Biotin (5:1), NeutrAvidin/Biotin-DNA (1:1) and cholesterol DNA tagged POPC-liposomes were added.

The bilayer structure enclosed a first volume of the detection volume and the volume not enclosed by the bilayer structure but within the detection volume is a second volume. The ratio between the first and second volumes was in this particular case about 0.1.

Melittin Binding and Pore Formation

Melittin solutions of various concentrations (0.5-40 μM) were injected over the bound liposomes in the Biacore® instrument at 5 μl/min. The change in response (RU) as a function of time (t) was fitted to $RU=RU_0+RU_1*(1-\exp(-t/\tau_1))+RU_2*(1-\exp(-t/\tau_2))$. However, the change in RU during the injection of 0.5 μM melittin could be described using only one exponential (i.e. $RU_2=0$). It is known that high concentrations of melittin can rupture cells and liposomes. Unspecific binding (i.e. binding to the biosensor surface without liposomes) of melittin was small, less than 5% of the binding of melittin to the liposome membrane surface (data not shown). The observed rate constant, $k_1$, ($k_1=1/\tau_1$) and the response ($RU_1$), were studied as a function of the concentration of melittin in the bulk solution $[Mel]_B$. The microscopic on-rate ($k_{+1}$) and off-rate ($k_{-1}$) of melittin with the liposome membrane surface were obtained from a fit of the data to $k_1=[Mel]_B*k_{+1}+k_{-1}$, which gave $k_{-1}=0.032$ s$^{-1}$ and $k_{+1}=3684$ M$^{-1}$ s$^{-1}$. The amplitude, $RU_1$, was also determined by the microscopic rate constants, $RU_1=RU_{max}*(k_{+1}/(k_{+1}+k_{-1}))$. There was a good fit of $RU_1$ as a function of $[Mel]_B$ when using $k_{-1}=0.032$ s$^{-1}$ and $k_{+1}=3684$ M$^{-1}$ s$^{-1}$ (which are obtained from the fit of $k_1$ as a function of $[Mel]_B$).

A comparison of the response (RU) from binding of liposomes to that from binding of melittin, gives the number of melittin molecules that binds to each liposome. It is known that the α-helical melittin molecule binds to the membrane in a parallel orientation and the area of the liposome membrane that a melittin molecule occupies is approximately 210 Å$^2$. The surface area of the liposome outer membrane is approximately 1.63*10^6 Å$^2$ (liposome radius≈360 Å). Hence the concentration of melittin at the liposome outer membrane ($[Mel]_{O.M.}$) and the fraction ($F_{O.M.}$) of the liposome surface that the melittin molecules cover can be calculated for each $[Mel]_B$.

At concentrations of 2, 4, 8 and 40 μM of melittin in the bulk solution, association of melittin with the liposome were biphasic. It is known that pore formation is induced at a threshold concentration of melittin at the membrane surface. If pores are formed, melittin molecules in the bulk solution outside the liposomes should be able to cross the liposome membrane and bind to the inner membrane surface of the liposomes. It is thus assumed that the slower kinetic phase represent melittin binding to the inner membrane. The observed rate constant, $k_2$, was found to be linear dependent on $[Mel]_B$ which shows that transfer a melittin through the pore is not the rate limiting step (not dependent on $[Mel]_B$). A linear fit gave that $k_{+2}=56$ M$^{-1}$ s$^{-1}$ and that $k_{-2}=0.0046$ s$^{-1}$. The lower value of the apparent diffusion coefficient $k_{+2}$ (56 M$^{-1}$ s$^{-1}$) compared to $k_{+1}$ (3684 M$^{-1}$ s$^{-1}$) can be explained by the lower probability of a melittin molecule finding the pores of the liposome than the liposome surface as a whole. The number of pores/liposome is Gaussian distributed and at low $[Mel]_{O.M.}$ an increase in $[Mel]_B$ increases the number of liposomes having one pore. Hence, at low $[Mel]_B$ the response ($RU_2$) will not only depend on $[Mel]_B$ but also on the fraction of liposomes that do not have any pores. At high $[Mel]_B$, where all liposomes have at least one pore, the surface coverage of melittin at the inner membrane should equal that at the outer membrane, and $RU_2$ should approach $RU_{2max}=RU_1*(Area_{In}/Area_{Out})$. Hence the above results show that the slower kinetic phase describes binding of melittin to the inner membrane. Further support comes from an observation that RU, after the injection of 4, 8 and 40 μM is stopped, does not return to the initial value (pre-injection), which is explained by the melittin molecules being trapped inside the liposomes as the pores disappear due to melittin dissociation from the membrane surface.

Melittin Pore Mediated Sucrose Uptake

A simple method for real-time and label-free uptake measurements of analytes across membranes at a biosensor surface would be of great value when investigating for example membrane transporters. Here we wanted to test if it was possible to measure the uptake of an analyte, sucrose, through the melittin pore by simply detecting the change in refractive index of the solution inside the liposome caused by the analyte as it is taken up.

FIG. 1 shows the successive addition of Neutravidin/Biotin DNA (N/B), 0.1 M sucrose (S1), 2 mg/ml cholesterol DNA tagged POPC-liposomes (POPC), 0.1 M sucrose (S2), 40 μM melittin, 0.1 M sucrose (S3), 0.1 M sucrose (S4), 0.1 M sucrose (S5) to a PEG/PEG-biotin functionalized surface.

Figure 2:
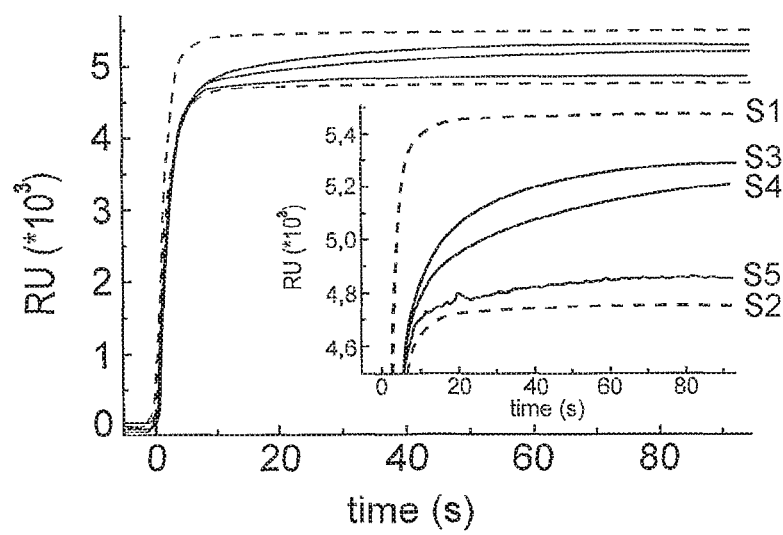
FIG. 2 shows the response (RU) from the five sucrose additions (S1-S5). The insert shows a partial enlargement of FIG. 2.

FIG. 2 shows the response (RU) from the five sucrose additions (S1-S5). Adding sucrose changes the refractive index of the solution in the detection volume, i.e. the volume corresponding to the evanescent field above the sensor surface, which is manifested as a shift in RU. The smaller increase in RU upon adding S2 compared to adding S1 corresponds to the reduced accessible volume of the evanescent field caused by the surface-bound liposomes. Addition of melittin produces pores in the liposomes membrane and hence makes the interior volume of the liposomes accessible to the added sucrose molecules. As the melittin addition is stopped, melittin dissociates from the membrane surface and the number of liposomes having melittin-pores decreases with time. FIG. 2 shows the change in RU upon addition of sucrose as the number of pores/liposome is reduced (S3-S5).

Figure 3:
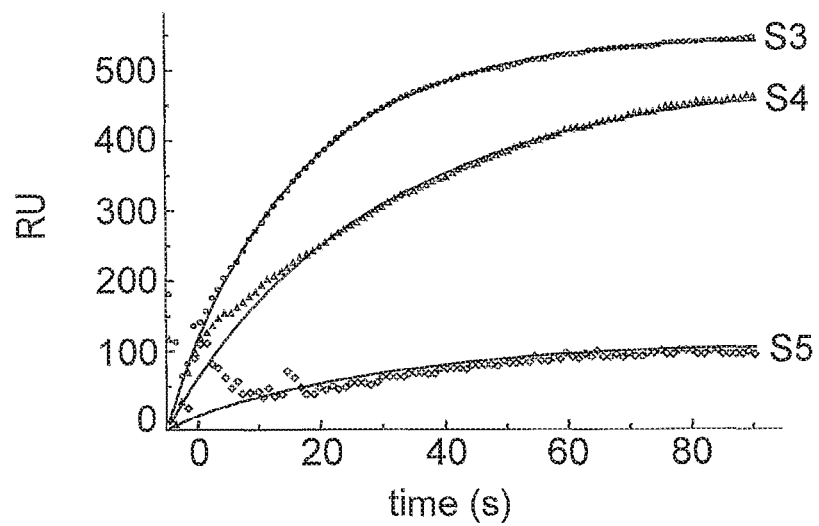
FIG. 3 shows the uptake of sucrose into the liposomes as a function of time, which is obtained by subtracting the change in RU upon addition of sucrose to closed liposomes (S2) from the change in RU upon addition of S3-S5.

FIG. 3 shows the uptake of sucrose into the liposomes as a function of time, which is obtained by subtracting the change in RU upon addition of sucrose to closed liposomes (S2) from the change in RU upon addition of S3-S5. The amplitude of the uptake decrease from S3 to S5, which is explained by a decreasing number of liposomes having pores. The rate also decreases from S3 to S5, which is explained by decreasing number of pores per liposome. From the graph in FIG. 3 the decay time for uptake of sucrose can be estimated and $\tau_3\approx20$ sec. Given that the concentration of sucrose inside the liposome after the uptake is equal to $[sucrose]_B=0.1$ M, then ~7400 sucrose molecules cross the membrane in ~20 sec. Table 2 show that $RU_2/RU_{2max}$ at $[Mel]B=40$ μM is 0.85 which correspond to the number of liposomes having more than one pore/liposome. The amplitude of the response is in good agreement with the value that can be expected from filling the liposomes with 0.1 M of sucrose, which have a molecular weight (Mw) of 0.34 kDa. The expected RU of the 7400 sucrose molecules (0.1 M) inside the liposome can be calculated from the obtained response of immobilizing the liposome itself (RU=6790). The Mw of the liposome is 35800 kDa, which gives 0.19 RU/kDa. The Mw of 7400 sucrose molecules is 7400*0.342 kDa=2531 kDa, which gives that RU=2531*0.19=480. Since only ~85% of the liposomes have pores the expected value is 480/0.85≈560 RU, which is in good agreement with the measured response of 530 RU from the S3 injection.

Example 2

SPR-Based Methods for Screening of Multiple Permeation Events by Investigating the Permeability of the Non-Electrolytes Glycerol, Urea and Hydroxyurea The efficiency of the SPR-based method and its compatibility with screening of multiple permeation events was evaluated by investigating the permeability of the non-electrolytes glycerol, urea and hydroxyurea, which are all biologically relevant molecules. For example, the efficiency by which glycerol is transported across the membranes of the adipocytes, where fat molecules are stored, has been suggested to be an important factor in the development of obesity and type II diabetes [17]. Urea, on the other hand, is a waste product in the metabolic process and is transported out from liver cells and released from the body via urine, while hydroxyurea is a drug that has been widely used in cancer chemotherapy [18] as well as in treatment of HIV-virus infections [19]. The applicability of the method is demonstrated for in situ alteration and simultaneous monitoring of liposome permeability by monitoring the increase in glycerol permeation upon a gradual cyclodextrin-induced reduction in the liposomal cholesterol content. Also shown is the compatibility of the method to probe transport of ions.

Figure 4B:
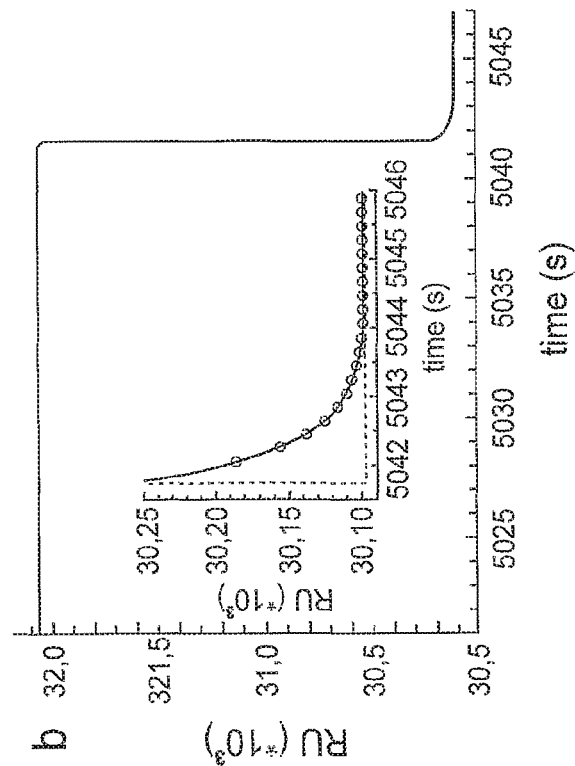
FIGS. 4a and 4b show liposome permeability for glycerol, urea and hydroxyurea.
Figure 4A:
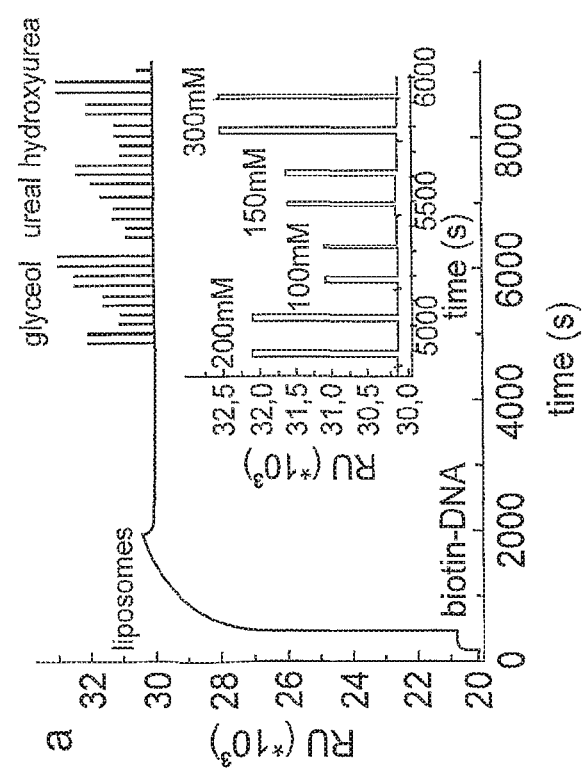

At first 70 nm liposomes were provided in accordance with Example 1. FIG. 4*a* shows binding of 70 nm liposomes followed by repeated injection pulses of glycerol, urea, hydroxyurea at different concentrations (see inset). FIG. 4*b* shows a magnification of one of the rinsing steps, upon which the solute (glycerol) is released from the liposome interior. Also shown in FIG. 4*b* (dashed curve) is an identical rinsing step without immobilized liposomes, illustrating that the time constant of the fluidic exchange is faster than 100 ms, which is sufficient to temporally resolve these transport measurements. The rate of glycerol release was examined in a temperature interval from 8 to 22° C. The results are demonstrated in FIG. 5*a*. In agreement with expectations, the rate of transport across the lipid membrane increases with increasing temperature, and Arrhenius plots display a linear dependence between ln(1/) and 1/T, yielding activation energies in excellent agreement with literature data for the three solutes (glycerol, urea and hydroxyurea) investigated, see FIG. 5*b*.

The results shown in FIGS. 4 and 5 demonstrate that the method can be used to accurately determine permeation coefficients of lipid membranes by following the release of solutes, rather than the uptake. Note that all these data were obtained from a single experiment using the same set of immobilized liposomes. The reproducibility between different experiments was better than 2%.

Figures 6A, 6B, 6C:
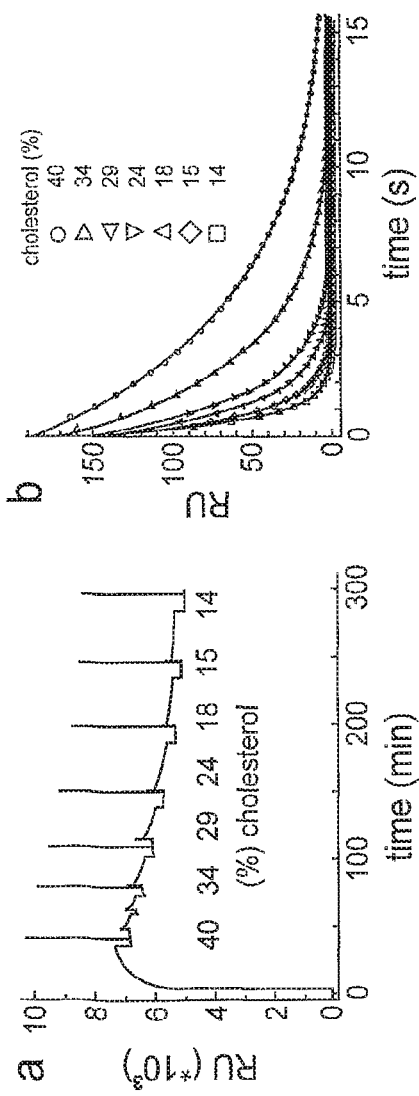
FIGS. 6a to 6c show the behaviour of cholesterol comprising liposomes when subjected to cyclodexterin.

70 nm liposomes containing 40% cholesterol were provided in accordance with Example 1. Binding of the liposomes followed by repeated injection cyclodextrin, which removes cholesterol from the lipid bilyaer of the liposomes is shown in FIG. 6*a*. The SPR response is proportional to the interfacial refractive index, which makes it possible to quantify the removal of cholesterol. After seven injections of cyclodextrin, the cholesterol content was reduced to 14%.

Each injection of cyclodextrin (FIG. 6*a*) was followed by an injection pulse of glycerol, which enabled the time constant of glycerol transport versus cholesterol content to be quantified, ranging from around 7 s at 40% cholesterol to 1 s at 14% cholesterol, see FIG. 6*b*. Note that a difference in transport rate was detectable for as little as 1% change in cholesterol content.

FIG. 6*c* shows the variations in permeability (estimated from the rate of solute transfer and the vesicle area) and the amplitude of the response (which is proportional to the internal volume). In agreement with expectations, the permeability decreases linearly versus cholesterol content, while the internalized volume increases non-linearly. The latter observation reflects a structural change of the membrane at a cholesterol content of around 25%.

Figure 7:
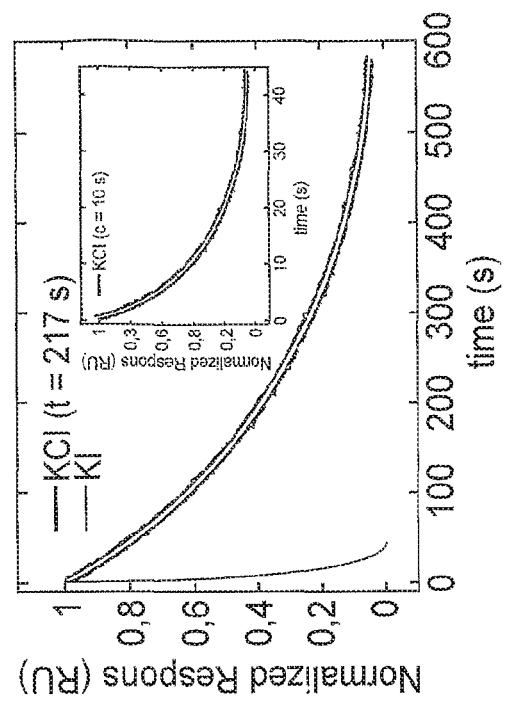
FIG. 7 illustrates membrane transport of iodide and chloride ions.
Figure 7:
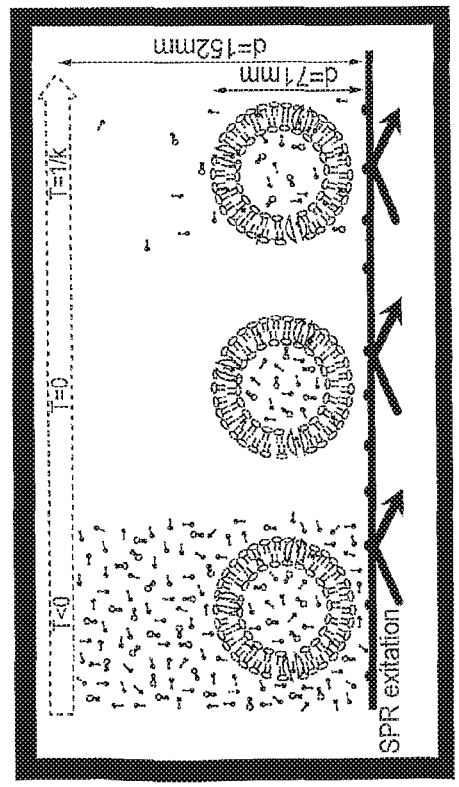

With the measurements shown in FIGS. 3*a* to *c*, it is demonstrated that the method enables solute transfer to be quantified in terms of permeability, which can simultaneously be correlated with structural changes of the membrane properties. Information of this type is of high relevance in studies on how, for example, drugs influence the permeability of cell-membranes. Both passive and membrane-protein mediated transfer of uncharged solutes is of high biological and pharmaceutical relevance. However, for a method like this to be generically applicable for any type of membrane transport reaction, also ion translocation should be possible to measure, which is today typically measured using patch-clamp based assays. FIG. 7 illustrates membrane transport of iodide (~10 s) and chloride (~200 s) ions, in excellent agreement with literature data. Note that gramicidin was incorporated into the liposomes in order to ensure co-transport of counter ions (K+), thus prohibiting the establishment of an electrostatic transmembrane potential that would otherwise restrict the unhindered transport of anions.

The results shown in FIG. 7 demonstrate the applicability of the method to time resolve membrane translocation reactions also of charged solutes. The natural extension of this work is studies of molecule and ion-channel controlled transport, of high relevance in the drug-screening process.

As illustrated for glycerol, urea and hydroxyurea, the method according to the invention enables screening of multiple permeation events in a single measurement, and allows for in situ alterations in permeability to be quantified, which is exemplified by successive removal of cholesterol from the lipid bilayer. In comparison with alternative methods to probe non-electrolyte transfer, which rely on indirect measurements osmotically-induced size changes of suspended liposomes, the method improves the sensitivity and reduces the required amount of sample by orders of magnitude.

In the set of results shown in FIGS. 4 to 7, it is demonstrated that solute transport across the lipid bilayer membrane of liposomes immobilized in an electromagnetic evanescent field can be determined by following the changes in refractive index of the liposome-internalized volume upon solute release, rather than uptake (FIG. 4). It is also demonstrated that the membrane properties can be varied in situ, and be correlated to changes in permeability (FIG. 5). In FIG. 6, we demonstrate that not only uncharged solutes, but also the transport of ions can be measured by following changes in the refractive index of the liposome-internalized volume upon solute release (or uptake).

In summary, the present invention admits the possibility of using this sensing principle for direct measurements of molecular transport of non-electrolyte solutes across membranes with a time resolution of 100 ms. The method is unique in the sense that it enables direct, rather than indirect (c.f. the DLS and fluorescence quenching methods), measurements of solute transfer across lipid bilayers, which was so far possible only for charged molecules using patch-clamp [14] or chip-based alternatives [15]. In comparison with the indirect methods, it also offers all other advantages of surface-based methods, such as rapid sequential (or parallel) screening of multiple solutes as well as in situ perturbation of liposome permeability by addition of effector molecules. There is also no limitation with respect to the size of the analyzed liposomes, while the DLS-based method is applicable on relatively large liposomes only, since liposomes with a diameter smaller than around 80 nm are essentially non-compressible (<1%) [16].

Although the invention has been described with regard to its preferred embodiments which comprise the best mode presently known to the inventors it should be understood that various changes and modifications as would be obvious to one having the ordinary skill in this art may be made without departing from the scope of the invention as set forth in the claims appended hereto.

REFERENCES

1. E. Vierteljahrsschrift der Naturforschenden Gesellschaft in Zürich: Overton, Vierteljahrsschrift der Naturforschenden Gesellschaft in Zürich 40, 159 (1895).
2. H. Danielli Davson, J. F., The Permeability of Natural Membranes. (Cambridge University Press, Cambridge, England, 1943).
3. P. Mueller, D. O. Rudin, H. T. Tien et al., Nature 194, 979 (1962).
4. A. D. Bangham, Prog Biophys Mol Biol 18, 29 (1968).
5. B. E. Cohen and A. D. Bangham, Nature 236 (5343), 173 (1972).
6. A. S. Verkman, J Membr Biol 148 (2), 99 (1995).
7. D. G. Levitt and H. J. Mlekoday, J Gen Physiol 81 (2), 239 (1983).
8. P. Y. Chen and A. S. Verkman, Pflugers Arch 408 (5), 491 (1987).
9. P. Y. Chen, D. Pearce, and A. S. Verkman, Biochemistry 27 (15), 5713 (1988).
10. U. Jonsson, L. Fagerstam, B. Ivarsson et al., Biotechniques 11 (5), 620 (1991).
11. L. S. Jung, C. T. Campbell, T. M. Chinowsky et al., Langmuir 14 (19), 5636 (1998).
12. B. Liedberg, I. Lundstrom, and E. Stenberg, Sensors and Actuators B-Chemical 11 (1-3), 63 (1993).
13. M. Branden, S. Dahlin, and F. Hook, Chemphyschem 9 (17), 2480 (2008).
14. E. Neher and B. Sakmann, Nature 260 (5554), 799 (1976).
15. A. Janshoff and C. Steinem, Analytical and Bioanalytical Chemistry 385 (3), 433 (2006).
16. S. T. Sun, A. Milon, T. Tanaka et al., Biochimica Et Biophysica Acta 860 (3), 525 (1986).
17. E. M. Wintour and B. A. Henry, Trends Endocrinol Metab 17 (3), 77 (2006).
18. C. Fausel, Am J Health Syst Pharm 64 (24 Suppl 15), S9 (2007).
19. F. Lori, A. Foli, L. M. Kelly et al., Curr Med Chem 14 (2), 233 (2007).

The invention claimed is:

1. A method comprising:
    contacting a bilayer structure with at least one agent to be analyzed, the bilayer structure being tethered to at least one metal surface and enclosing a detection volume;
    detecting a change in refractive index only in the detection volume enclosed by the bilayer structure resulting from transportation of the at least one agent across a membrane of the bilayer structure; and
    determining a rate at which the at least one agent is transported across the bilayer structure using the detected change in the refractive index of the detection volume.

2. The method of claim 1 wherein the bilayer structure comprises at least one liposome.

3. The method of claim 2 wherein the at least one liposome is tethered to the at least one metal surface with a spacer molecule.

4. The method of claim 1 wherein at least one of a membrane protein or an ionophore is associated with the bilayer structure.

5. The method of claim 4 wherein the bilayer structure comprises at least one liposome.

6. The method of claim 5 wherein the at least one liposome is tethered to the at least one metal surface with a spacer molecule.

7. The method of claim 1 wherein the bilayer structure comprises at least two layers of liposomes.

8. The method of claim 1 wherein the change in refractive index is detected with a surface plasmon resonance sensor, an ellipsometry sensor, or an optical waveguide laser spectroscopy sensor.

9. A method comprising:
    contacting a bilayer structure with at least one agent to be analyzed, the bilayer structure being tethered to at least one metal surface and enclosing a detection volume;
    detecting a change in refractive index only in the detection volume enclosed by the bilayer structure resulting from transportation of the at least one agent across a membrane of the bilayer structure; and
    determining a permeation coefficient using the detected change in the refractive index of the detection volume.

10. The method of claim 9 wherein the bilayer structure comprises at least one liposome.

11. The method of claim 10 wherein the at least one liposome is tethered to the at least one metal surface with a spacer molecule.

12. The method of claim 9 wherein at least one of a membrane protein or an ionophore is associated with the bilayer structure.

13. The method of claim 12 wherein the bilayer structure comprises at least one liposome.

14. The method of claim 13 wherein the at least one liposome is tethered to the at least one metal surface with a spacer molecule.

15. The method of claim 9 wherein the bilayer structure comprises at least two layers of liposomes.

16. The method of claim 9 wherein the change in refractive index is detected with a surface plasmon resonance sensor, an ellipsometry sensor, or an optical waveguide laser spectroscopy sensor.

17. A method comprising:
    contacting a bilayer structure with at least one agent to be analyzed, the bilayer structure being tethered to at least one surface and enclosing a detection volume;
    detecting a change in refractive index only in the detection volume enclosed by the bilayer structure resulting from transportation of the at least one agent across a membrane of the bilayer structure, the change in refractive index being detected with a surface plasmon resonance sensor, an ellipsometry sensor, or an optical waveguide laser spectroscopy sensor; and determining a rate at which the at least one agent is transported across the bilayer structure using the detected change in the refractive index of the detection volume.

18. The method of claim 17 wherein the bilayer structure comprises at least one liposome.

19. The method of claim 18 wherein the at least one liposome is tethered to the at least one surface with a spacer molecule.

20. The method of claim 17 wherein at least one of a membrane protein or an ionophore is associated with the bilayer structure.

21. The method of claim 20 wherein the bilayer structure comprises at least one liposome.

22. The method of claim 21 wherein the at least one liposome is tethered to the at least one surface with a spacer molecule.

23. The method of claim 17 wherein the bilayer structure comprises at least two layers of liposomes.

24. A method comprising:
  contacting a bilayer structure with at least one agent to be analyzed, the bilayer structure being tethered to at least one surface and enclosing a detection volume;
  detecting a change in refractive index only in the detection volume enclosed by the bilayer structure resulting from transportation of the at least one agent across a membrane of the bilayer structure, the change in refractive index being detected with a surface plasmon resonance sensor, an ellipsometry sensor, or an optical waveguide laser spectroscopy sensor; and
  determining a permeation coefficient using the detected change in the refractive index of the detection volume.

25. The method of claim 24 wherein the bilayer structure comprises at least one liposome.

26. The method of claim 25 wherein the at least one liposome is tethered to the at least one surface with a spacer molecule.

27. The method of claim 24 wherein at least one of a membrane protein or an ionophore is associated with the bilayer structure.

28. The method of claim 27 wherein the bilayer structure comprises at least one liposome.

29. The method of claim 28 wherein the at least one liposome is tethered to the at least one surface with a spacer molecule.

30. The method of claim 24 wherein the bilayer structure comprises at least two layers of liposomes.

* * * * *